United States Patent [19]

Yoshida et al.

[11] Patent Number: 4,756,847

[45] Date of Patent: Jul. 12, 1988

[54] 4'-CYANO-3'-HALOGENOPHENYL 4-(5-SUBSTITUTED-PYRIMIDIN-2-YL)BENZOATE DERIVATIVES AND LIQUID CRYSTAL COMPOSITION COMPRISING SAME

[75] Inventors: Naoyuki Yoshida, Kamakurashi; Kisei Kitano, Yokohamashi; Yoshito Furukawa, Yokohamashi; Tetsuya Ogawa, Yokohamashi; Shigeru Sugimori, Fujisawashi; Yasuyuki Goto, Yokohamashi; Toyoshiro Isoyama, Yokohamashi; Kazunori Nigorikawa, Yokohamashi, all of Japan

[73] Assignee: Chisso Corporation, Osaka, Japan

[21] Appl. No.: 817,274

[22] Filed: Jan. 8, 1986

[30] Foreign Application Priority Data

Jan. 18, 1985 [JP] Japan .................... 60-7144

[51] Int. Cl.$^4$ .......... C09K 3/34; G02F 1/13; C07D 239/32
[52] U.S. Cl. .......... 252/299.61; 252/299.67; 252/582; 544/335
[58] Field of Search .......... 544/335; 252/299.61, 252/299.67, 582

[56] References Cited

U.S. PATENT DOCUMENTS 4,311,610  1/1982  Zaschke et al. .................... 544/335
4,533,488  8/1985  Fukui et al. ........................ 544/335

FOREIGN PATENT DOCUMENTS 56-53661   5/1981  Japan .................... 544/335
56-164169 12/1981  Japan .................... 544/335
56-164170 12/1981  Japan .................... 544/335
56-164171 12/1981  Japan .................... 544/335

OTHER PUBLICATIONS

Scheuble et al., CA, vol. 104, 1986, (Abstract D.E. 3,404,117, Aug. 8, 1985), 104: 59,500.
Krause et al., CA, vol. 106, 1987, (Abstract D.E. 3,515,373, Nov. 6, 1986), 106: 93766.

Primary Examiner—Richard A. Schwartz
Assistant Examiner—J. G. Mullins
Attorney, Agent, or Firm—Leydig, Voit & Mayer

[57] ABSTRACT

Novel compounds which, when used as a components of liquid crystal compositions, have good compatibility with other components and also have large values of dielectric anisotropy and optical anisotropy, and liquid crystal compositions containing the same are provided, which compounds are 4'-cyano-3'-halogenophenyl 4-(5-substituted-pyrimidin-2-yl)benzoate expressed by the formula

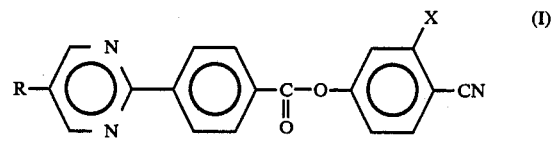

wherein R represents an alkyl group of 1 to 10 carbon atoms or $-(CH_2)_m-O-(CH_2)_p-CH_3$ wherein m and p each represent an integer of 0 to 8 and $m+p \leq 8$, and X represents a halogen atom.

9 Claims, No Drawings

4'-CYANO-3'-HALOGENOPHENYL 4-(5-SUBSTITUTED-PYRIMIDIN-2-YL)BENZOATE DERIVATIVES AND LIQUID CRYSTAL COMPOSITION COMPRISING SAME

BACKGROUND OF THE INVENTION

This invention relates to novel organic compounds and more particularly it relates to novel liquid crystal compounds useful as a components of liquid crystal materials.

As well known, liquid crystal compounds have been used for various display devices, making use of specific properties of the compounds in their liquid crystal phases such as dielectric anisotropy, refractive anisotropy, etc. These display devices refer to liquid crystal display elements using the electro-optic effect, thermo-optic effect or other optical effects of liquid crystals, along with advancements in electronics, a number of liquid crystal compounds have been used for liquid crystal display elements employing the field effects such as twisted nematic effect, guest-host effect, etc.

For these liquid crystal materials, however, there is no single substance which endures practical use with respect of its various characteristics such as mesomorphic range, operation voltage, response properties, etc.; thus it is the present status that practically, several kinds of liquid crystal compounds have been mixed together or the compounds have been mixed with several kinds of non-liquid crystal compounds to obtain materials which can endure practical use.

Recently a liquid crystal display element capable of being driven at low voltages has been required more and more, and in order to fulfill such a requirement, a liquid crystal composition having a large dielectric anisotropy value (hereinafter referred to as $\Delta\epsilon$) has been desired.

In general, in order to obtain such a liquid crystal composition having a large $\Delta\epsilon$, a component having as large a $\Delta\epsilon$ as possible may be used, but in this case it is necessary for the component to have a good compatibility with other components and also to broaden or at least not to narrow the mesomorphic range of the resulting composition.

Further, a liquid crystal composition having a large optical anisotropy value ($\Delta n$) can inhibit occurrence of color unevenness caused by partially non-uniform distance between the substrates of a liquid crystal display element and also can reduce the distance between the substrates; hence such a composition has an advantage that the field intensity of a cell using the composition can be enhanced even when the same voltage is impressed. Thus, a compound having a large $\Delta n$ has been desired.

SUMMARY OF THE INVENTION

The present invention aims at solving the above-mentioned problems.

A first object of the present invention is to provide novel compounds usable as a constituting components of a liquid crystal compositions and also to provide liquid crystal compound which have as large a $\Delta\epsilon$ and a $\Delta n$ as possible, and when used together with other components, have good compatibility therewith and further at least does not reduce the mesomorphic range.

A second object of the present invention is to provide liquid crystal compositions containing a novel liquid crystal compound and having a large $\Delta\epsilon$ and $\Delta n$.

The present invention in a first aspect resides in a 4'-cyano-3'-halogenophenyl 4-(5-substituted-pyrimidin-2-yl)benzoate (hereinafter referred to as compound of the present invention) expressed by the formula

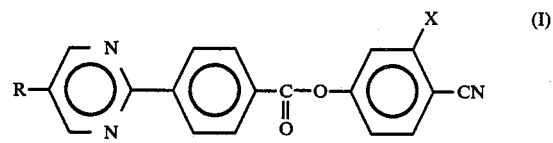

wherein R represents an alkyl group of 1 to 10 carbon atoms or $-(CH_2)_m-O-(CH_2)_p-CH_3$ wherein m and p each represent an integer of 0 to 8 and $m+p \leq 8$, and X represents a halogen atom.

Further the present invention in a second aspect resides in a liquid crystal composition having at least two components at least one of which is a 4'-cyano-3'-halogenophenyl 4-(5-substituted-pyrimidin-2-yl)benzoate expressed by the above formula (I).

DESCRIPTION OF PREFERRED EMBODIMENTS

Concrete examples of the alkyl group as R in the formula (I) of the present invention are linear chain alkyl groups such as methyl, ethyl, propyl, butyl, pentyl, hexyl, heptyl, octyl, nonyl and decyl, and branched chain alkyl groups such as isopropyl, 1-methylpropyl, 2-methylpropyl, 1-methylbutyl, 2-methylbutyl, 3-methylbutyl, 1-methylpentyl, 1-ethylpentyl, 2-methylpentyl, 1-methylhexyl, 2-ethylhexyl, 1-methylheptyl, etc. Concrete examples of alkyloxy group as R are methoxy, ethoxy, propoxy, butoxy, pentyloxy, hexyloxy, heptyloxy, octyloxy and nonyloxy. Further, concrete examples of the alkoxy-substituted alkyl group as R are methoxymethyl, ethoxymethyl, propoxymethyl, etc. As the halogen atom, F or Cl may be exemplified.

As a typical preparation of the compound of the present invention, the following reaction scheme may be illustrated:

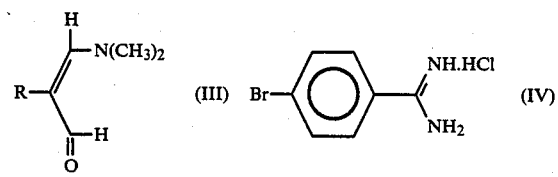

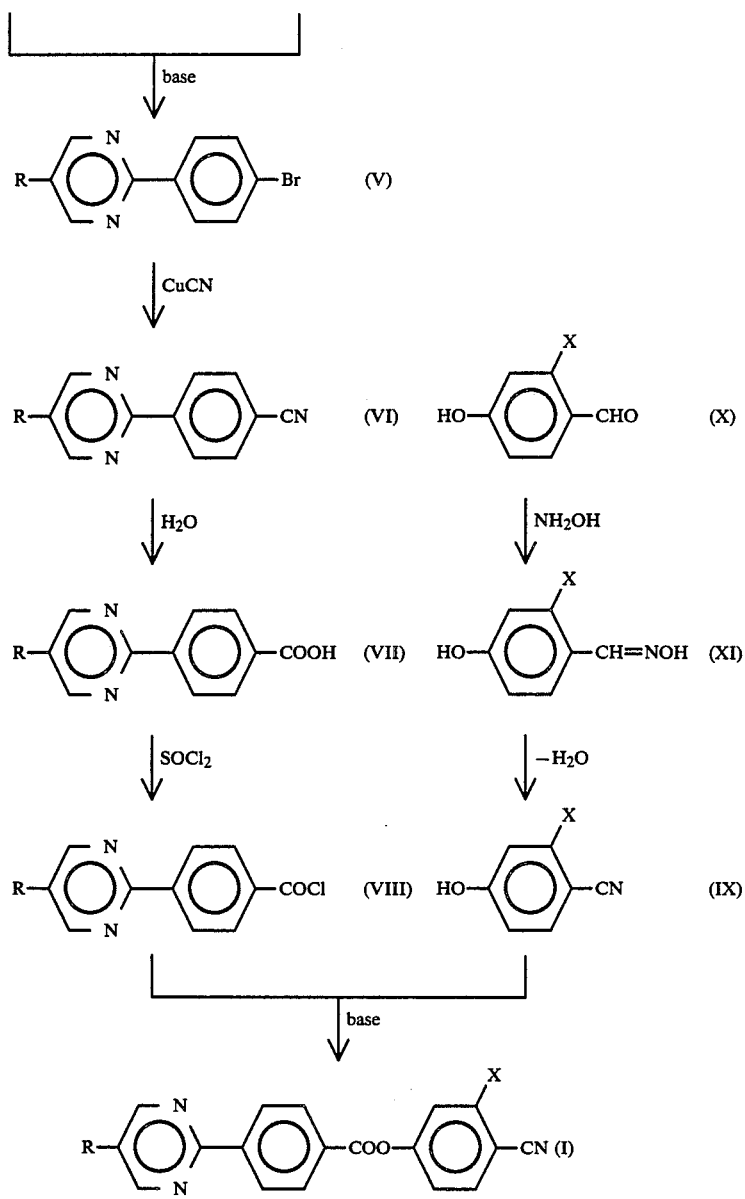

Namely, an α-substituted-β-dimethylaminoacrolein (III) and bromobenzamidine hydrochloride (IV) are subjected to cyclization reaction with a suitable base such as sodium methoxide, NaOH, pyridine, etc. to obtain a pyrimidine compound (V), followed by converting the Br group of (V) into CN group with cuprous cyanide and further hydrolyzing the CN group to obtain a pyrimidinylbenzoic acid (VII), which is then reacted with thionyl chloride to obtain an acid chloride (VIII), which is then reacted with a 4-cyano-3-halogenophenol (IX) obtained by converting a 2-halogeno-4-hydroxybenzaldehyde (X) into an oxime (XI) with hydroxylamine and then dehydrating this oxime with e.g. acetic anhydride, to obtain the compound of the present invention i.e. a 4′-cyano-3′-halogenophenyl 4-(5-substituted-pyrimidine-2-yl)benzoate (I).

The liquid crystal compositions of the present invention preferably contain a compound of the present invention of the formula (I) at a level of 1 to 30% by weight, preferably 3 to 20% by weight. If the level of the compounds of the present invention is less than 1% by weight, the contribution to the dielectric anisotropy is small, while if the level exceeds 30% by weight, the viscosity of the composition may increase and thereby reduce the practical properties.

Examples of existing liquid crystal compounds with which the compounds of the present invention can be used to give the liquid crystal compositions of the present invention are expressed by the following general formulae (i) to (xxxiii):

In these formulae, X represents

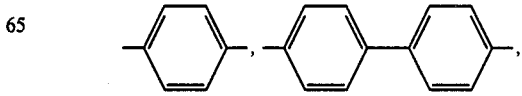

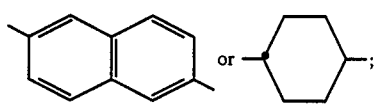
Y represents —CN, —R', halogeno, or —COO—X—Y', Y' represents —CN, —R' or —OR'; and R and R' each represent an alkyl group.
Furthermore, usable compounds also include those wherein one hydrogen atom in the benzene ring(s) of such compounds is substituted by a halogen atom such as F.
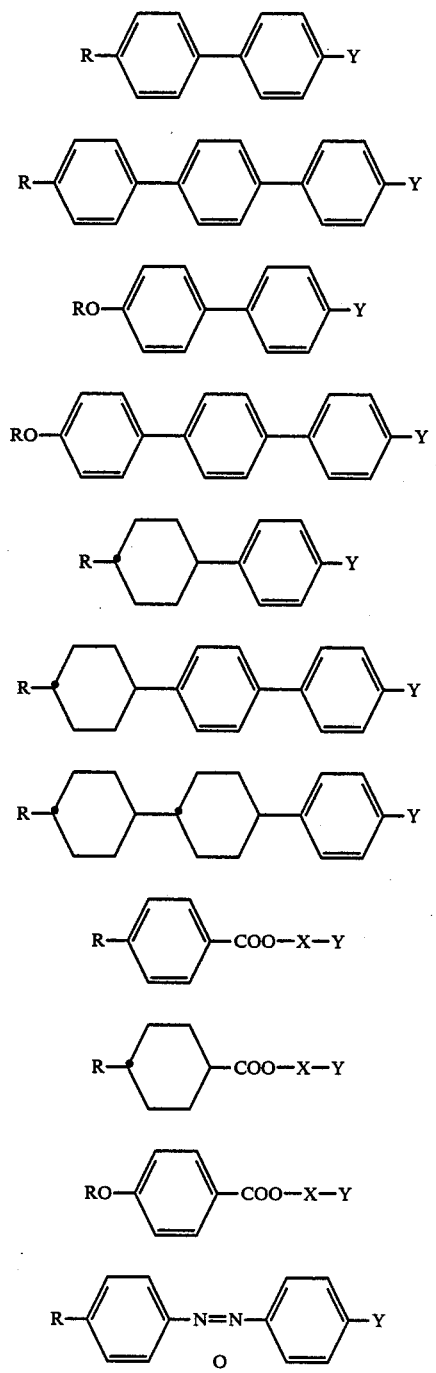

7
-continued

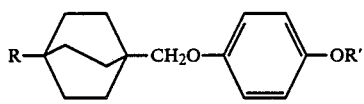 (xxv)

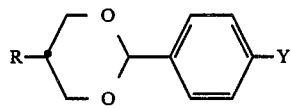 (xxvi)

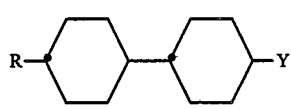 (xxvii)

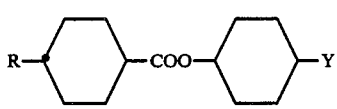 (xxviii)

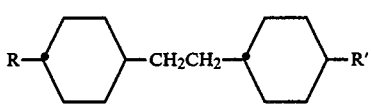 (xxix)

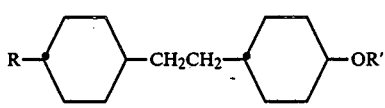 (xxx)

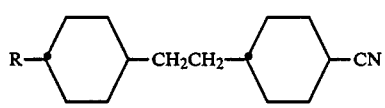 (xxxi)

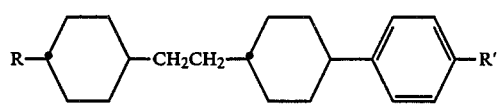 (xxxii)

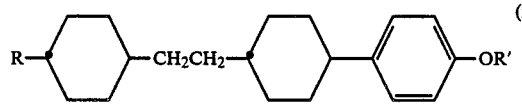 (xxxiii)

The effectiveness of the compound of the present invention is as follows:

Firstly, it has become possible to provide novel compounds which, when used as a component of liquid crystal compositions, has a good compatibility with other components.

Secondly the compounds of the present invention have a very large $\Delta\epsilon$. For example, 4'-cyano-3'-fluorophenyl 4-(5-ethylpyrimidin-2-yl)benzoate of the present invention has a $\Delta\epsilon$ as large as 69.2 which was obtained from the value of a mixture thereof with phenylcyclohexane liquid crystals according to extrapolation method. Thus, the compounds are useful as a component of liquid crystal compositions, which, when added in a small quantity to other components, can raise the $\Delta\epsilon$ of the resulting liquid crystal composition, and also can reduce the driving voltage of liquid crystal display elements utilizing the liquid crystal composition.

Thirdly, the compounds of the present invention have a high nematic-isotropic liquid phase transition point (hereinafter abbreviated to N-I point) and also have a large $\Delta n$.

8

Further the effectiveness of the compositions of the present invention are as follows:

Firstly it has become possible to provide liquid crystal compositions containing a novel compounds, which compositions has never been seen.

Secondly the compositions has a large $\Delta\epsilon$ and $\Delta n$.

Thirdly the composition has a high N-I transition point.

Fourthly, by utilizing the compositions of the present invention, it is possible to obtain a liquid crystal display element having a low driving voltage.

The present invention will be described in more detail by way of Examples.

EXAMPLE 1

4'-Cyano-3'-fluorophenyl 4-(5-ethylpyrimidin-2-yl)benzoate 4-(5-Ethylpyrimidin-2-yl)benzoyl chloride (1.1 g, 0.004 mol) and 4-cyano-3-fluorophenol (0.6 g, 0.004 mol) were dissolved in pyridine (5 ml) and heated with stirring for one hour, followed by allowing the solution to stand overnight, adding toluene (50 ml), pouring the mixture in water, washing the resulting toluene layer with 2N-hydrochloric acid, 2N-NaOH aqueous solution and purified water in this order, drying the toluene layer and distilling off toluene under reduced pressure to obtain white crystals, which were then recrystallized from n-heptane to obtain the objective 4'-cyano-3'-fluorophenyl 4-(5-ethylpyrimidin-2-yl)benzoate (0.8 g, 0.002 mol, yield 50%). This product had a crystalline-smectic point (C-S point) of 140.8° C., a smectic-nematic point (S-N point) of 142.0° C. and a N-I point of 231.3° C. The analytical values of C and H were C: 69.1% and H: 4.2% (calculated values, C: 69.15% and H: 4.06%).

The NMR values were as follows:

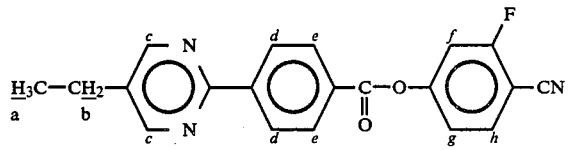

a: 1.37 ppm 3H, b: 2.75 ppm 2H, c: 8.69 ppm 2H, d, e: 8.26, 8.60 ppm 4H, f, g: 7.29 ppm 2H, h: 7.72 ppm 1H.

EXAMPLE 2

4'-Cyano-3'-fluorophenyl 4-(5-butylpyrimidin-2-yl)benzoate was obtained in the same manner as in Example 1. This product had a C-S point of 115.9° C., a S-N point of 134.5° C. and a N-I point of 214.1° C. The analytical values of C and H were as follows: C: 70.4% and H: 4.8% (calculated values, C: 70.39% and H: 4.83%).

EXAMPLE 3

4'Cyano-3'-fluorophenyl 4-(5-propylpyrimidin-2-yl)benzoate was obtained in the same manner as in Example 1. This product had a C-S point of 118.1° C., a S-N point of 130.6° C. and a N-I point of 228.0° C. The analytical values of C and H were as follows: C: 69.8% and H: 4.4% (calculated values, C: 69.79% and H: 4.46%).

EXAMPLE 4 (USE EXAMPLE)

A liquid crystal composition (A) consisting of

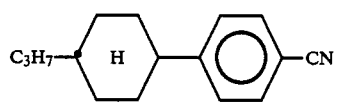 30 parts by weight,

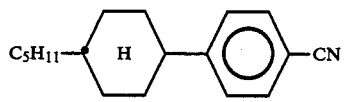 40 parts by weight and

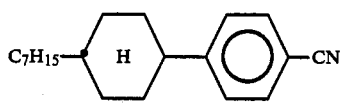 30 parts by weight, has a N-I point of 52.1° C., a Δε of 11.2 and a Δn of 0.119.

To this liquid crystal composition (A) (95 parts by weight) was added 4'-cyano-3'-fluorophenyl 4-(5-ethylpyrimidin-2-yl)benzoate of Example 1 of the present invention (5 parts by weight). The resulting liquid crystal composition had a N-I point raised to 58.2° C., and also had a large increase of Δε and Δn to 14.1 and 0.124, respectively.

EXAMPLE 5 (USE EXAMPLE)

In the same manner as in Example 4, to the liquid crystal composition (A) (90 parts by weight) was added 4'-cyano-3'-fluorophenyl 4-(5-butylpyrimidin-2-yl)benzoate of Example 2 of the present invention (10 parts by weight). The resulting liquid crystal composition had a N-I point raised to 62.5° C. and also had a large increase of Δε and Δn to 15.8 and 0.130, respectively.

EXAMPLE 6 (USE EXAMPLE)

In the same manner as in Example 4, to the liquid crystal composition (A) (90 parts by weight) was added 4'-cyano-3'-fluorophenyl 4-(5-propylpyrimidin-2-yl)benzoate of Example 3 of the present invention (10 parts by weight). The resulting liquid crystal composition had a N-I point raised to 63.8° C. and also had a large increase of Δε and Δn to 15.6 and 0.134, respectively.

What we claim is:

1. A 4'-cyano-3'-halogenophenyl 4-(5-substituted-pyrimidin-2-yl)benzoate expressed by the formula

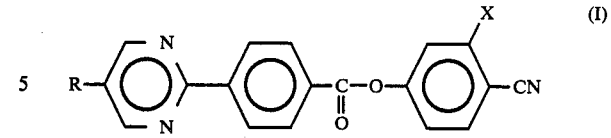

wherein R represents an alkyl group of 1 to 10 carbon atoms or $-(CH_2)_m-O-(CH_2)_p-CH_3$ wherein m and p each represent an integer of 0 to 8 and $m+p \leq 8$, and X represents a halogen atom.

2. A 4'-cyano-3'-fluorophenyl 4-(5-alkoxypyrimidin-2-yl)benzoate according to claim 1 wherein R represents an alkyloxy group of 1 to 9 carbon atoms.

3. A 4'-cyano-3'-fluorophenyl 4-(5-alkoxyalkyl-pyrimidin-2-yl)benzoate according to claim 1 wherein R represents an alkoxyalkyl group of $-(CH_2)_m-O-(CH_2)_p-CH_3$ wherein m and p each represent an integer of 1 to 7 and $m+p \leq 8$.

4. A 4'-cyano-3'-fluorophenyl 4-(5-alkylpyrimidin-2-yl)benzoate according to claim 1 wherein R represents an alkyl group of 1 to 10 carbon atoms.

5. A 4'-cyano-3'-halogenophenyl 4-(5-butylpyrimidin-2-yl)benzoate according to claim 1 wherein X represents a fluorine or chlorine atom.

6. A 4'-cyano-3'-halogenophenyl 4-(5-propylpyrimidin-2-yl)benzoate according to claim 1 wherein X represents a fluorine or chlorine atom.

7. A 4'-cyano-3'-halogenophenyl 4-(5-ethylpyrimidin-2-yl)benzoate according to claim 1 wherein X represents a fluorine or chlorine atom.

8. A liquid crystal composition comprising at least one first substance having liquid crystal properties and at least one second substance which is a 4'-cyano-3'-halogenophenyl 4-(5-substituted-pyrimidin-2-yl)benzoate expressed by the formula (1) set forth in claim 1, said at least one second substance being present in an amount sufficient to enhance dielectric anisotropy.

9. A liquid crystal composition comprising at least one first substance having liquid crystal properties and at least one second substance which is a 4'-cyano-3'-halogenophenyl-4-(5-substituted-pyrimidin-2-yl)benzoate expressed by the formula

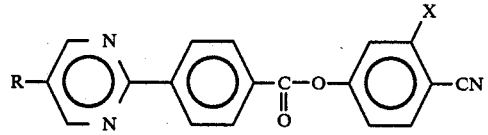

wherein R represents an alkyl group of 1 to 10 carbon atoms or $-(CH_2)_m-O-(CH_2)_p-CH_3$ wherein m and p each represent an integer of 0 to 8 and $m+p \leq 8$, and X represents a halogen atom, said at least one second substance being present in an amount of about 1 to about 30%, by weight.

* * * * *